(12) United States Patent  
Eigler et al.

(10) Patent No.: US 8,142,363 B1  
(45) Date of Patent: Mar. 27, 2012

(54) CARDIAC RHYTHM MANAGEMENT LEAD WITH OMNI-DIRECTIONAL PRESSURE SENSING

(75) Inventors: Neal L. Eigler, Pacific Palisades, CA (US); James S. Whiting, Los Angeles, CA (US); Brian M. Mann, Edgartown, MA (US); Werner Hafelfinger, Thousand Oaks, CA (US); Xiangqun Chen, Valencia, CA (US); Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 1139 days.

(21) Appl. No.: 11/776,225

(22) Filed: Jul. 11, 2007

(51) Int. Cl.  
*A61B 5/02* (2006.01)  
*A61N 1/00* (2006.01)

(52) U.S. Cl. ........ 600/488; 600/483; 600/485; 600/486; 607/6

(58) Field of Classification Search .................. 600/485, 600/486, 488; 73/715–728; 607/116, 119, 607/122, 127  
See application file for complete search history.

(56) References Cited

U.S. PATENT DOCUMENTS

| 3,815,611 | A | | 6/1974 | Denniston, III | |
|---|---|---|---|---|---|
| 5,964,714 | A | * | 10/1999 | Lafontaine | 600/561 |
| 6,296,615 | B1 | * | 10/2001 | Brockway et al. | 600/486 |
| 7,162,926 | B1 | * | 1/2007 | Guziak et al. | 73/729.2 |
| 7,684,872 | B2 | * | 3/2010 | Carney et al. | 607/116 |
| 2002/0120200 | A1 | * | 8/2002 | Brockway et al. | 600/488 |
| 2004/0176828 | A1 | * | 9/2004 | O'Brien | 607/119 |
| 2005/0159800 | A1 | * | 7/2005 | Marshall et al. | 607/122 |
| 2005/0288596 | A1 | * | 12/2005 | Eigler et al. | 600/485 |
| 2008/0269623 | A1 | * | 10/2008 | Ruben | 600/488 |

* cited by examiner

*Primary Examiner* — Patricia Mallari  
*Assistant Examiner* — Eric Messersmith

(57) ABSTRACT

Embodiments include a cardiac rhythm management system having a lead that includes an omni-directional pressure sensor that is configured to resist tissue in-growth and provide reliable and consistent pressure readings from within a patient's vasculature. Embodiments of the cardiac rhythm management lead may also include a variety of pacing and shocking electrodes.

17 Claims, 10 Drawing Sheets

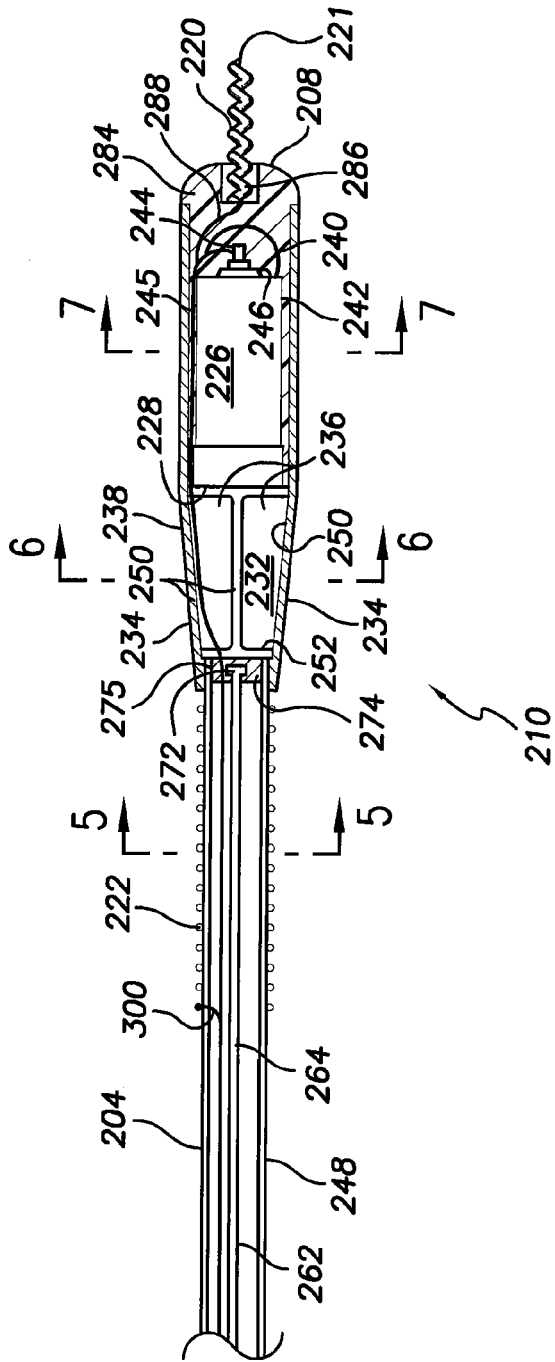
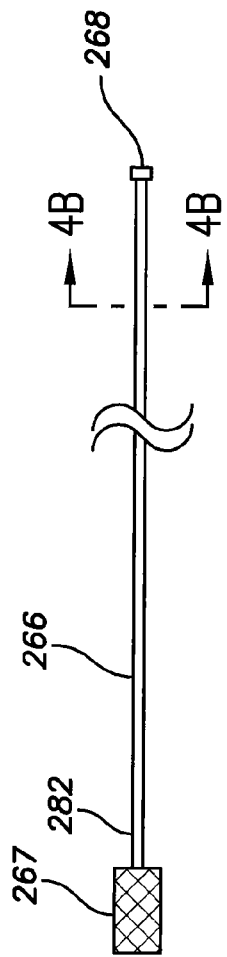
FIG. 4
FIG. 4A
FIG. 4B

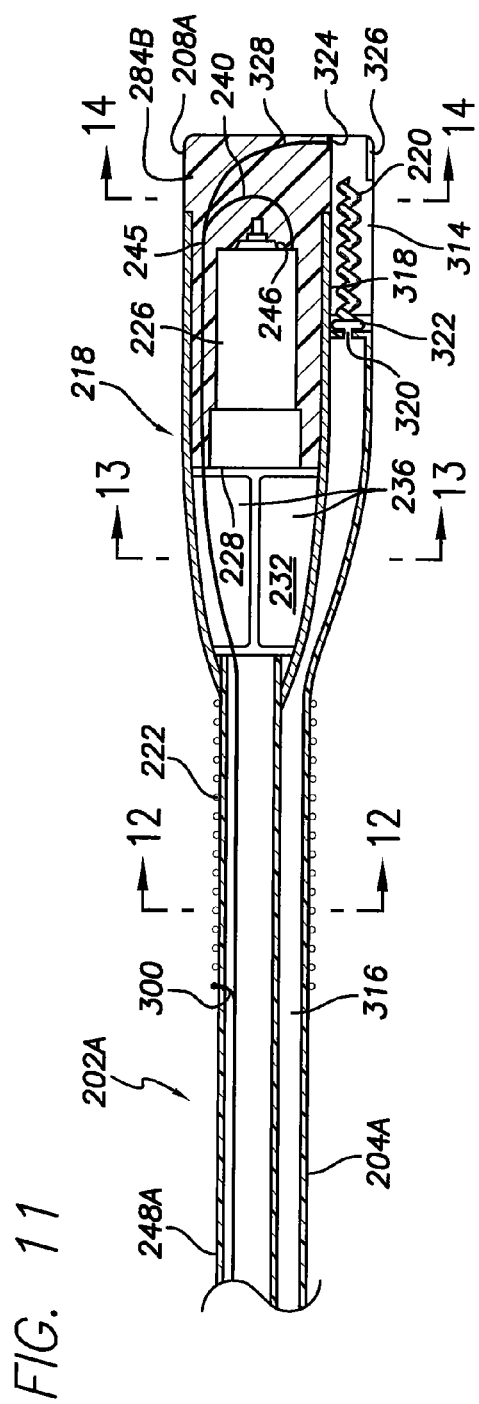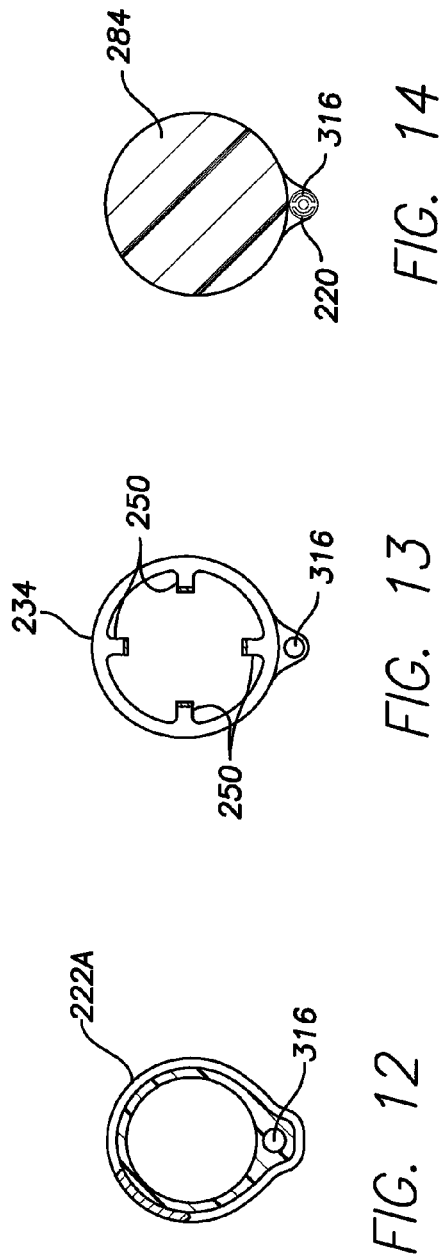
FIG. 11
FIG. 12
FIG. 13
FIG. 14

CARDIAC RHYTHM MANAGEMENT LEAD WITH OMNI-DIRECTIONAL PRESSURE SENSING

FIELD OF THE INVENTION

Embodiments discussed herein relate to implantable medical devices such as implantable electrical stimulation devices including pacemakers, implantable cardioverter/defibrillators (ICDs) and the like and the leads used in conjunction with such devices. More specifically, the leads may include at least one omni-directional pressure sensor configured to sense pressure within a patient's body. Some embodiments are directed to cardiac rhythm management systems that may include an implantable stimulation device coupled to a lead with omni-directional pressure sensing capability and one or more electrodes that may be configured to apply pacing or shocking therapies to a patient's heart.

BACKGROUND

Body implantable leads may be used to provide a communication or therapy signal link between stimulation devices, such as a cardiac pacemaker, and target body tissue, such as tissue of the heart, which is to be electrically stimulated or observed by sensing or other means. The leads connecting pacemakers with the tissue of the heart may be used for pacing or for sensing electrical signals produced by the heart, or for both pacing and sensing in which case a single electrical lead serves as a bi-directional pulse transmission link between the pacemaker and the heart.

Some cardiac rhythm management indications may benefit from the use of pressure sensing capabilities incorporated into stimulation device and lead embodiments. Pressure sensors may be located in the body of a cardiac rhythm management lead, rather than at the distal end. Such a configuration may be used for measuring right ventricle (RV) pressure from an ICD lead where the distal end typically is an active fixation pacing electrode. However, incorporating this type of pressure sensor into the body of an RV defibrillation lead between the distal shock coil and the distal pacing electrode creates several problems. For example, such pressure sensitive diaphragms are sensitive to tissue contact and may produce tissue impact artifacts or pressure damping including sensor drift due to thick tissue overgrowth. In addition, in order to safely deliver such a lead to a target tissue site within a patient's heart, it is desirable to maximize flexibility of the distal section of the lead. For the configuration described, the entire distal portion of the lead including the transducer and screw in electrode create an extended rigid section, increasing the difficulty of lead placement and the likelihood of lead perforation.

What has been needed are cardiac rhythm management systems that are configured to provide electrical stimulation therapy or electrical sensing in conjunction with pressure sensing with leads that are flexible and easy to deploy and resistant to drift in pressure sensing measurements over time after deployment.

SUMMARY

Some embodiments of an implantable cardiac rhythm management lead with pressure sensing, include an elongate flexible lead body having a distal portion, distal end, a proximal end and a longitudinal axis. A tissue engaging member is disposed at the distal end of the lead body and an electrode is disposed on the distal section of the lead body. A pressure transducer assembly is disposed on the distal section of the lead body having a pressure transducer with a pressure sensitive surface, an volume adjacent the pressure sensitive surface enclosed by a frame structure having an omni-directional aperture disposed substantially about a circumference of the lead body to allow pressure signal waves to enter the volume from outside the lead and interact with the pressure sensitive surface of the transducer.

Some embodiments of an implantable pressure sensing lead include an elongate flexible lead body having a distal portion, distal end, a proximal end and a longitudinal axis. A distal tissue engaging member configured as a helical electrode having a sharp tissue penetrating distal tip is disposed at and extending from the distal end of the lead body. A pressure transducer assembly is disposed on the distal section of the lead body having a pressure transducer with a pressure sensitive surface, an volume adjacent the pressure sensitive surface enclosed by a frame structure having an omni-directional aperture disposed substantially about a circumference of the lead body to allow pressure signal waves to enter the volume from outside the lead and interact with the pressure sensitive surface of the transducer. A first large surface area shocking electrode is disposed on the lead body proximal of the pressure transducer assembly and a second large surface area shocking electrode is disposed on the lead body proximal of the first large surface area shocking electrode.

Some embodiments of an implantable cardiac rhythm management system with pressure sensing include an elongate flexible lead body having a distal portion, distal end, a proximal end and a longitudinal axis. A tissue engaging member is disposed at the distal end of the lead body. An electrode is disposed on the distal section of the lead body. A pressure transducer assembly is disposed on the distal section of the lead body having a pressure transducer with a pressure sensitive surface, an volume adjacent the pressure sensitive surface enclosed by a frame structure having an omni-directional aperture disposed substantially about a circumference of the lead body to allow pressure signal waves to enter the volume from outside the lead and interact with the pressure sensitive surface of the transducer. An implantable stimulation device is coupled to the lead and configured to monitor pressure and provide electrical cardiac stimulation signals to the electrode to manage a cardiac rhythm of the patient.

Some embodiments of a method of managing the cardiac rhythm of a patient include providing an implantable cardiac rhythm management lead having an elongate flexible lead body with a distal portion, distal end, a proximal end and a longitudinal axis. A tissue engaging member of the lead is disposed at the distal end of the lead body. An electrode is disposed on the distal section of the lead body. A pressure transducer assembly is disposed on the distal section of the lead body having a pressure transducer with a pressure sensitive surface, an volume adjacent the pressure sensitive surface enclosed by a frame structure having an omni-directional aperture disposed substantially about a circumference of the lead body to allow pressure signal waves to enter the volume from outside the lead and interact with the pressure sensitive surface of the transducer. Once provided, the lead is advanced within a patient's heart until a distal portion of the lead is disposed adjacent target tissue of the patient's body. The tissue engaging member is then secured to tissue in the patient's heart and an electrical cardiac rhythm management signal is conducted from the electrode to the target tissue of the patient's heart. Pressure from within the patient's heart is also omni-directionally sensed substantially about a circumference of the distal section of the lead.

These features of embodiments will become more apparent from the following detailed description when taken in conjunction with the accompanying exemplary drawings.

BRIEF DESCRIPTION OF THE DRAWINGS

FIG. 4 is an enlarged view in partial section of the encircled portion of the lead of the system of FIG. 3 taken along lines 4-4 of FIG. 3.

FIGS. 4A and 4B illustrate an embodiment of a stylet that may be used to apply torque to the distal portion of the lead of FIG. 4.

FIG. 11 is an elevational view in partial section of a distal portion of an embodiment of a lead having a retractable tissue engaging member.

FIG. 12 is a transverse cross sectional view of the lead of FIG. 11 taken along lines 12-12 of FIG. 11.

FIG. 13 is a transverse cross sectional view of the lead of FIG. 11 taken along lines 13-13 of FIG. 11.

FIG. 14 is a transverse cross sectional view of the lead of FIG. 11 taken along lines 14-14 of FIG. 11.

DETAILED DESCRIPTION

Some embodiments of cardiac rhythm management systems or components thereof discussed herein relate to or include cardiac pacing methods, cardiac sensing methods and associated devices designed to relieve a variety of conditions that result from cardiac disease as well as other conditions. Cardiac rhythm management systems that include pressure sensing capability may also include stimulation devices, such as implantable stimulation devices that may be used to generate stimulation therapy signals in conjunction with pressure signal data taken from the leads of such cardiac rhythm management systems. As such, an overview of stimulation device embodiments that may be used with embodiments of the cardiac rhythm management systems and components thereof follows.

Overview of Stimulation Device Embodiments

Figure 1:
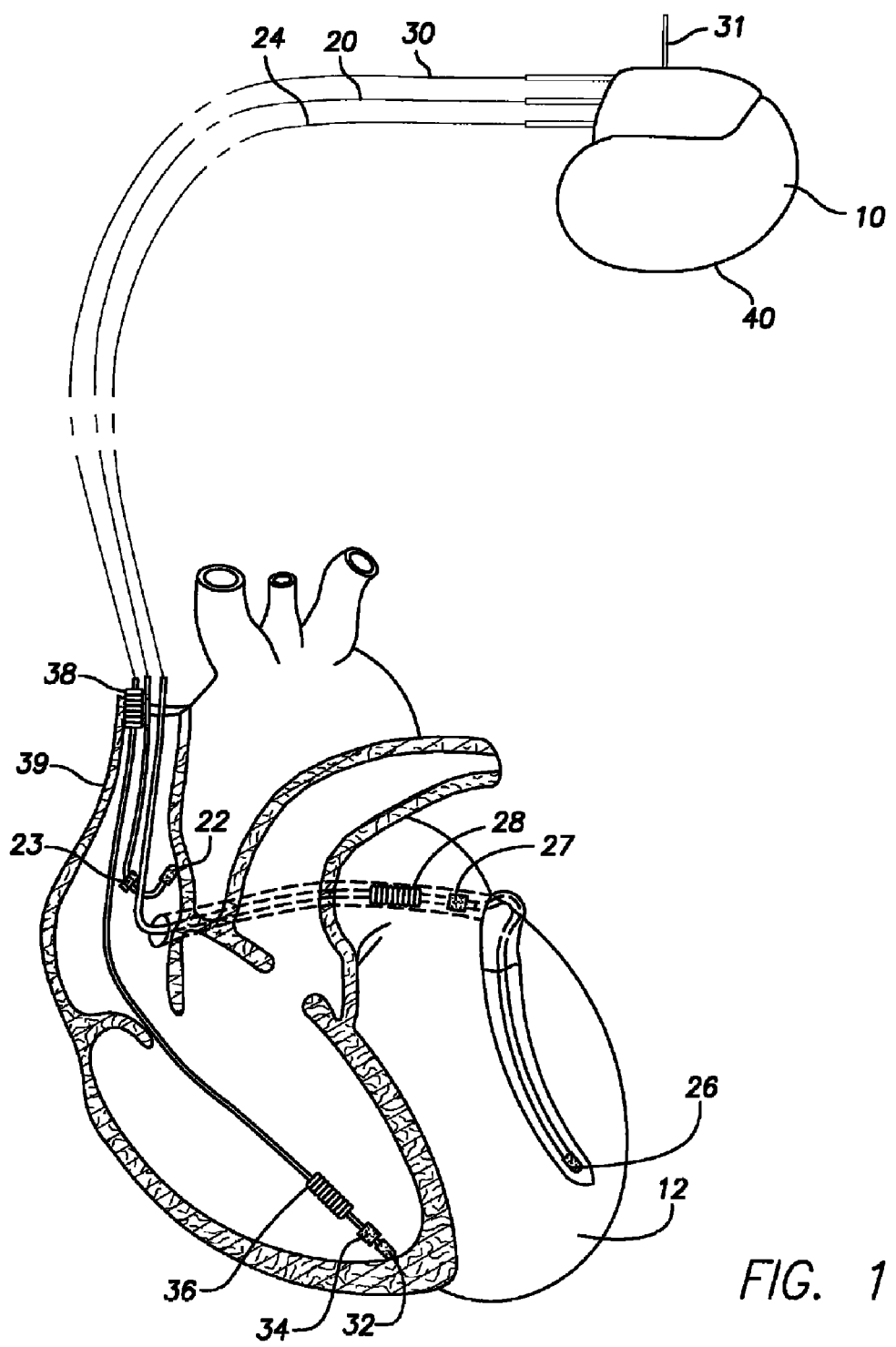
FIG. 1 is a simplified diagram illustrating an implantable cardiac stimulation device in electrical communication with at least three electrical leads implanted into the heart of a patient.

FIG. 1 shows a stimulation device 10 in electrical communication with the heart 12 of a patient with three electrical leads, 20, 24 and 30, in a configuration suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava 39. Accordingly, the right ventricular lead 30 is capable of receiving cardiac signals, and delivering stimulation in the form of pacing and shock therapy to the right ventricle. The stimulation device 10 includes an outer housing 40 that may be electrically conductive.

Figure 2:
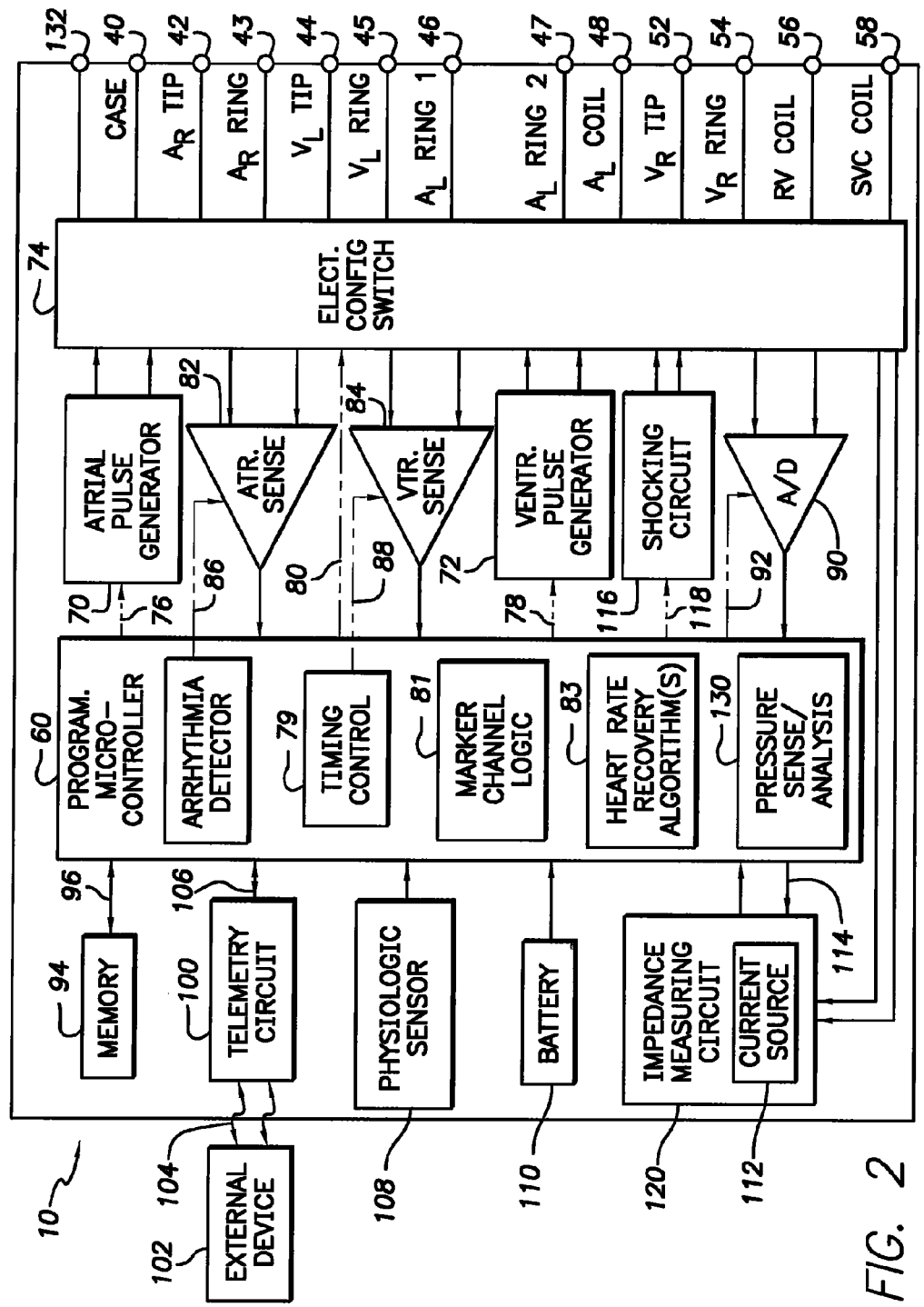
FIG. 2 is a functional block diagram of a multi-chamber implantable stimulation device illustrating exemplary basic elements of a stimulation device which can provide cardioversion, defibrillation, and/or pacing stimulation in up to four chambers of the heart.

As illustrated in FIG. 2, a simplified block diagram is shown of the multi-chamber implantable cardiac stimulation device 10, which is capable of treating both fast and slow arrhythmias with stimulation therapy, including cardioversion, defibrillation, and pacing stimulation. While a particular multi-chamber device is shown, this is for illustration purposes only, and appropriate circuitry may be duplicated, eliminated or disabled in any desired combination to provide a device capable of treating the appropriate chamber(s) with cardioversion, defibrillation and pacing stimulation. In addition, some processing step embodiments discussed below may be implemented in the form of software instructions that are resident on a computer-readable media that is included with the stimulation device 10.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 45, 46, 47, 48, 52, 54, 56 and 58 (shown schematically and, for convenience, the names of the electrodes to which they are connected are shown next to the terminals). While it is recognized that the number of terminals of current devices may be limited due to international standards, some terminals/electrodes may be programmably eliminated/selected in order to accommodate various embodiments. In addition, standards may change in the future and accommodate additional configurations.

To achieve right atrial sensing and pacing, the connector includes at least a right atrial tip terminal ($A_R$ TIP) 42 and a right atrial ring terminal ($A_R$ RING) 43, adapted for connection to the atrial tip electrode 22 and atrial ring electrode 23, respectively. To achieve left chamber sensing, pacing and shocking, the connector includes a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a controller in the form of a programmable microcontroller 60, which controls the various modes of stimulation therapy. The microcontroller 60 (also referred to herein as a controller or control unit) includes a microprocessor, or equivalent control circuitry, designed specifically for detecting sensed cardiac function data, generating warning signals that may be felt, heard or seen by a patient, controlling delivery of stimulation therapy as well as other function and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein. Microprocessor-based control circuits for performing timing and data analysis functions may be used.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. In order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 also includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, blanking intervals, noise detection windows, evoked response windows, alert intervals, marker channel timing (via marker channel logic 81), etc. Some embodiments of the microcontroller 60 are programmed with one or more heart rate recovery algorithms 83. The heart rate recovery algorithm(s) operate to monitor a patient's heart rate recovery when, for example, the patient recovers from a period of exercise to a period of rest. The algorithms can then save data associated with the heart rate recovery.

Switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, combipolar, etc.) and various shocking vectors by selectively closing the appropriate combination of switches (not shown). Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. The atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches. In this way, the clinician may program the sensing polarity independent of the stimulation polarity.

Each sensing circuit, 82 and 84, preferably employs one or more low power, precision amplifiers with programmable gain and/or automatic gain control, band pass filtering, and a threshold detection circuit to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the stimulation device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia or other clinical condition. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). The atrial and ventricular sensing circuits 82 and 84 receive control signals over signal lines 86 and 88 from the microcontroller 60, for controlling gain, threshold, polarization charge removal circuitry, and the timing of any blocking circuitry coupled to the inputs of the atrial and ventricular sensing circuits 82 and 84.

Cardiac signals may also be applied to the inputs of an analog-to-digital (A/D) data acquisition system 90. The data acquisition system 90 may be configured to acquire intracardiac electrogram signals, convert the raw analog data into a digital signal, and store the digital signals for later processing and/or telemetric transmission to an external device 102. The microcontroller 60 enables the data acquisition system 90 via control signal 92 to sample the cardiac signal that falls within a capture detection window. The data acquisition system 90 is coupled to the right atrial lead 20, the coronary sinus lead 24, and the right ventricular lead 30 through the switch 74 to sample cardiac signals across any pair of desired electrodes. The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 allows intracardiac electrograms and status information relating to the operation of the device 10 (as contained in the microcontroller 60 or memory 94) to be sent to the external device 102 through an established communication link 104.

In some embodiments, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). A physiological parameter of the heart, which may be measured to optimize such pacing and to indicate when such pacing may be inhibited or terminated is the stroke volume of the heart. Accordingly, the microcontroller 60 responds by adjusting the various pacing parameters (such as rate, AV Delay, V-V Delay, etc.) at which the atrial and ventricular pulse generators, 70 and 72, generate stimulation pulses. A common type of rate responsive sensor is an activity sensor, such as an accelerometer or a piezoelectric crystal, which is mounted within the housing 40 of the stimulation device 10. While shown as being included within the stimulation device 10, the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may use lithium/silver vanadium oxide batteries.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. The microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38, as shown in FIG. 1. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, the device 10 is shown as having an impedance measuring circuit 120 including an impedance measuring current source 112 and a voltage measuring circuit 90 (shown in FIG. 2 as an A/D converter), which may be enabled by the microcontroller 60 via a control signal 114 for providing stroke volume measurements of the heart 12. The current source 112 can provide an alternating or pulsed excitation current. The voltage measuring circuitry 90 may also take the form of, for example, a differential amplifier. The uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring a respiration parameter (for example, tidal volume, respiration rate, minute ventilation or volume, abnormal or periodic breathing); measuring thoracic impedance for determining shock thresholds and shock timing (corresponding to the diastolic time); detecting when the device has been implanted; measuring a cardiac parameter (such as, stroke volume, wall thickness, left ventricular volume, etc.); and detecting the opening of the valves etc.

Cardiac Rhythm Management System

Embodiments of cardiac rhythm management systems discussed herein may be used for pacing, sensing, defibrillation, and pressure sensing within a patient's heart. Such systems may be used for treating a variety of indications including administration of cardiac resynchronization therapy. These systems may include stimulation devices, such as implantable stimulation devices 10, and leads which are configured to be coupled to the stimulation devices. Leads for such a cardiac rhythm management systems may include standard lead features such as electrodes, signal conducting conduits, such as insulated wires, and a tissue engaging member to secure the lead or a portion thereof to tissue. The lead may also include a pressure transducer having a pressure sensitive surface surrounded by a frame structure. The frame structure may optionally be filled with a pressure transmitting material such as a gel or polymer that will serve to transmit pressure waves or signals from a position or location outside the frame structure to the pressure sensitive surface of the transducer. This allows the pressure transducer to sense pressure waveforms propagating from all or most radial orientations relative to the lead while not increasing the length of the rigid section of the distal lead tip. This configuration also protects the pressure sensitive surface of the pressure transducer from direct contact with tissue and tissue ingrowth which may reduce the accuracy of pressure measurements or produce unwanted noise in pressure measurement signals.

The pressure transducer may be oriented with the diaphragm facing in a proximal direction or distal direction depending on the optimum location to measure pressure. For some embodiments, the pressure transducer may be pre-assembled and hermetically sealed within a housing which is generally cylindrical in shape and includes of an end facing sensor diaphragm and sensor electronics. Such a lead may also include a tissue engaging member which may also serve as a distal pacing electrode. A tissue engaging member in the form of a helical tissue penetrating electrode may be used for some embodiments of the lead.

Figure 3:
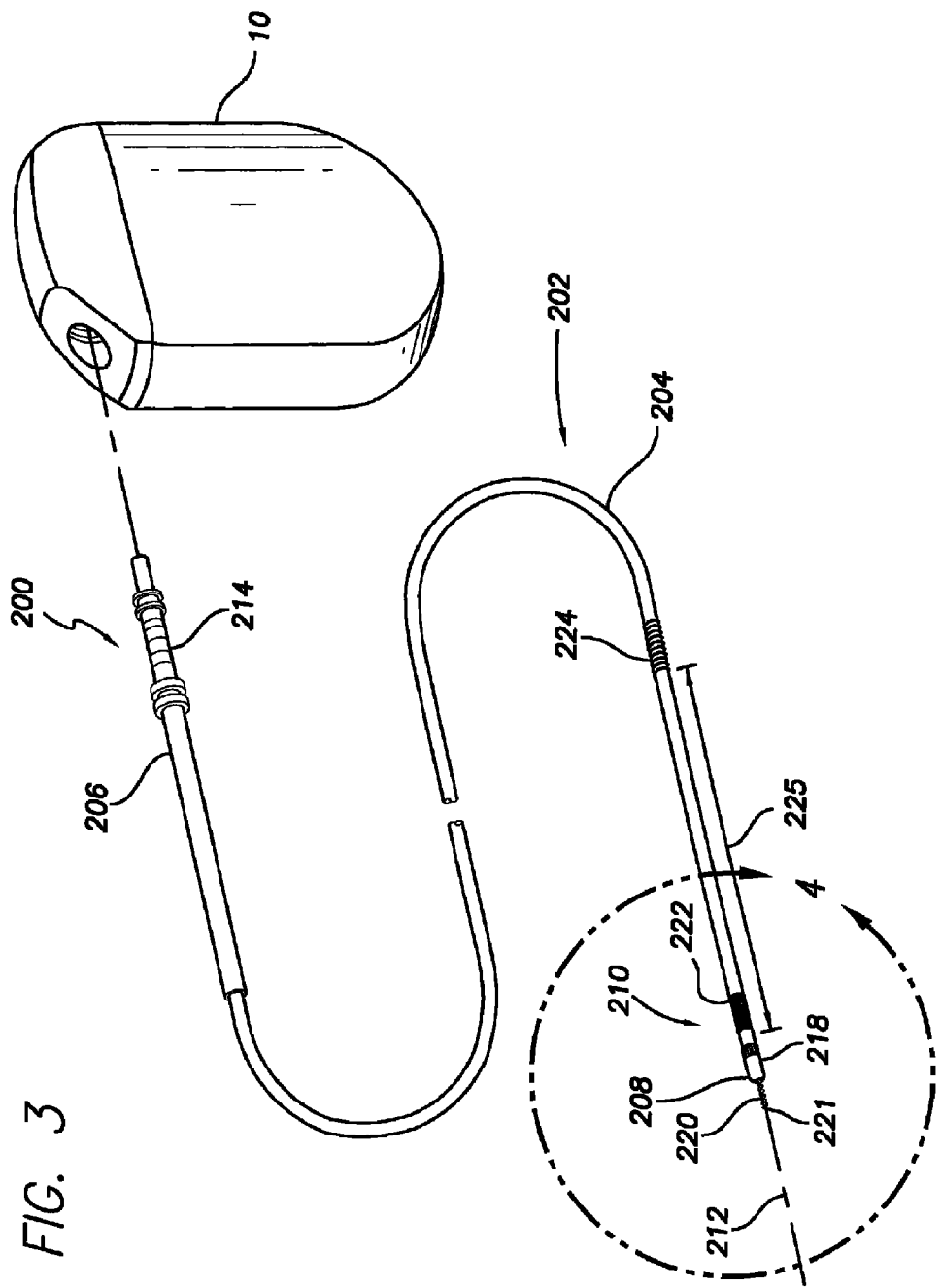
FIG. 3 is an exploded perspective view of a cardiac rhythm management system having omni-directional pressure sensing capability.

FIG. 3 illustrates an embodiment of a cardiac rhythm management system 200 for delivering electrical stimulation energy to target tissue of a patient and for monitoring pressure from a position on a distal section of a lead of the system 200. The system 200 includes a stimulation device 10, which may be an implantable stimulation device 10, and an implantable pressure sensing lead 202 configured to be coupled to the stimulation device 10 which may be used as a right ventricle defibrillation lead for some indications. The lead 202 includes an elongate flexible lead body 204 with a proximal end 206, distal end 208, distal section 210 and a longitudinal axis 212. A proximal connector 214 is disposed on the proximal end of the lead body 204 and is configured to be sealingly and electrically coupled to a receptacle 216 of the stimulation device 10. A pressure transducer assembly 218 is disposed on a distal section 210 of the lead body 204 and a distal tissue engaging member 220 configured as a helical electrode having a sharp tissue penetrating distal tip 221 is disposed at and extends from the distal end 208 of the lead body 204.

A first or distal shocking electrode or coil 222 having sufficient surface area for cardioversion therapy, defibrillation therapy and the like, is disposed on the lead body 204 just proximal of the pressure transducer assembly 218. The distal shocking electrode 222 may have the same or similar functions, features and dimensions as those of the right ventricular coil electrode 36 discussed above. A second or proximal shocking electrode or coil 224 is disposed on the lead body 204 proximal of the distal shocking electrode 222. The proximal shocking electrode may have the same or similar functions, features and dimensions as those of the SVC coil electrode 38 discussed above. A distal end of the distal shocking electrode 222 may be axially separated from a distal end of the proximal shocking electrode along the longitudinal axis 212 of the lead body 204 by a predetermined distance as indicated by arrow 225. The predetermined distance 225 may be about 5 cm to about 15 cm for some embodiments. The stimulation device 10 shown in FIG. 3 may have some or all of the features and methods of operation as discussed above in addition to the capability of processing one or more pressure signals from any of the pressure transducer embodiments of the lead embodiments discussed herein, as well as others. Pressure wave output signals may be conducted by a signal conducting conduit, such as insulated wire, from an output terminal of the pressure transducer 226 to the corresponding conductive terminal on the proximal connector 214, and, ultimately, to the appropriate pressure sense terminal 132 and pressure sense/analysis signal processing circuitry 130 of the stimulation device 10.

FIGS. 4-7 show an enlarged view of a distal portion of the lead 202. Referring to FIG. 4, the pressure transducer assembly 218 is disposed on the distal section 210 of the lead body 204 and includes a pressure transducer 226 with a pressure sensitive surface 228, a volume 232 adjacent the pressure sensitive surface 228 enclosed by a frame structure 234 having an omni-directional aperture 236 disposed substantially about an entire circumference of the lead body 204, and, more specifically, disposed substantially about the entire circumference of the frame structure 234. The aperture 236 is configured to allow pressure signals or pressure waves to enter the volume 232 from a position outside the lead 202 and interact with the pressure sensitive surface 228 of the transducer 226.

The pressure transducer embodiment 226 shown has a cylindrical outer shape that fits within a distal portion of the frame structure 234. The distal portion of the frame structure 234 may have an outer transverse dimension or diameter of about 3 mm to about 5 mm for some embodiments. The pressure transducer 226 may be secured to the frame structure 234 by adhesive bonding, soldering, welding or any other suitable method. The pressure sensitive surface 228 of the pressure transducer 226 faces a substantially proximal direction and is also substantially perpendicular to the longitudinal axis 212 of the distal portion the lead 202. The pressure sensitive surface 228 also forms a distal boundary for the volume 232 enclosed by the frame structure 234.

For some embodiments, an outer casing or housing 238 of the pressure transducer 226 may be electrically conductive and used as a distal ring electrode having the same or similar features and method of operation as ring electrode 34 discussed above. For such embodiments, the housing 238 of the pressure transducer 226 may be coupled to the stimulation device 10 by a signal conducting conduit 240, such as an insulated wire, that extends between and in electrical contact with the housing 238 and a corresponding conductive terminal on the proximal connector 214. This conductive terminal will in turn be coupled to the appropriate signal generating circuitry of the stimulation device 10. At a terminal end 242 of the transducer 226 axially opposite the pressure sensitive surface 228, an output terminal 244 extends from a ceramic feed through 246 of the pressure transducer 226. Pressure wave output signals generated as a result of pressure waves interacting with the pressure sensitive surface 228 of the pressure transducer 226 are conducted within the pressure transducer 226 circuitry to the output terminal 244. The output signals may then be carried by a signal conducting conduit, such as insulated wire 245, from the output terminal 244 to the corresponding conductive terminal on the proximal connector 214, and, ultimately, to the appropriate pressure sense terminal 132 and pressure sense/analysis signal processing circuitry 130 of the stimulation device 10.

The pressure transducer 226 may be encapsulated in a polymeric lead covering material, such as Silastic® that may be used to insulate the pressure transducer 226, electrically or otherwise, and help protect the pressure transducer 226 from the ingress of body fluids of the patient. If the pressure transducer housing 238 is to be used as a distal ring electrode, it may be desirable to leave of portion of the transducer housing 238 exposed without the polymeric covering to allow transmission of electrical signals through that exposed portion from the housing 238 to surrounding tissue.

The frame structure 234 may be made of any suitable high strength biocompatible material, such as stainless steel, titanium, NiTi alloys, MP35N, cobalt chromium alloys or the like. The frame structure 234 may also be coated with or partially formed from a radiopaque metal such as gold, tungsten, platinum, tantalum or the like in order to facilitate imaging of the distal portion of the lead 202 during deployment of the lead 202 to the desired location within the patient's body. The frame structure 234 forms a generally tubular shape that may have a continuous tubular wall structure in a more distal portion thereof that surrounds the pressure transducer 226 and a more proximal portion that surrounds and is secured to a distal end of a flexible tubular member 248 of the lead body 204. The aperture 236 in the frame structure 234 is formed by a gap in the frame structure 234 that is bridged by one or more thin struts 250 that extend from a more distal portion of the frame structure 234 to a proximal portion of the frame structure 234.

The struts 250 may be formed from a thin portion or portions of the frame structure 234 extending axially in a substantially longitudinal direction. For some embodiments, 2, 3, 4 or 5 struts 250 may be used to span the omni-directional aperture 236 in a longitudinal orientation. The struts 250 are thin enough and adequately spaced so as to provide a sufficient aperture 236 to allow pressure signals around the distal section 210 of the lead 202 to enter the volume 232 from substantially any circumferential orientation or direction relative to the distal section and propagate through the volume 232 from the aperture 236 to the pressure sensitive surface 228 of the pressure transducer 226. The volume 232 adjacent the pressure sensitive surface 228 of the pressure transducer 226 may vary in total volume. For some embodiments, the volume 232 may have a transverse dimension or diameter that is substantially similar to a transverse dimension or diameter of the frame structure 234 adjacent the pressure sensitive surface 238. The volume may have a length of about 0.5 times to about 5 times the transverse dimension or diameter of the volume 232, for some embodiments.

Figure 4C:
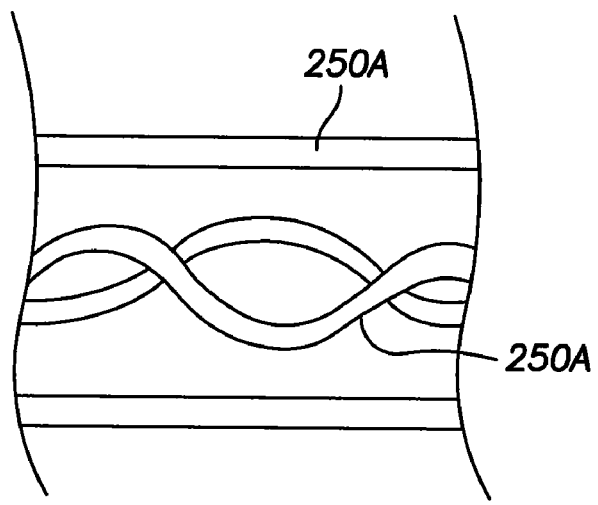
FIGS. 4C and 4D illustrate alternative strut embodiments for frame structures of a pressure sensor assembly.
Figure 4D:
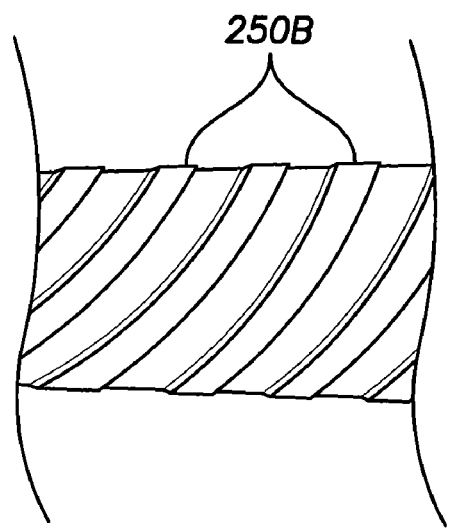
Figure 5:
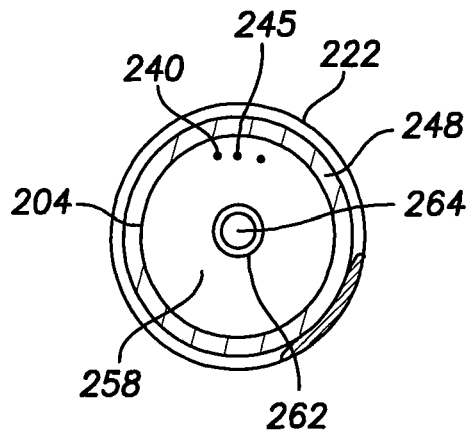
FIG. 5 is a transverse cross sectional view of the lead of FIG. 4 taken along lines 5-5 of FIG. 4.

Although the struts 250 are thin, they may also be sufficiently stiff and strong to provide adequate mechanical integrity and structure of the pressure transducer assembly 218 to prevent significant longitudinal bending of the frame structure 234 and pressure transducer assembly 218 as a whole. However, for some pressure transducer assembly embodiments 218, it may be desirable for the struts 250 to be configured to allow for longitudinal flexibility of the assembly 218. FIGS. 4C and 4D illustrate strut embodiments 250A and 250B, respectively, that provide longitudinal flexibility to the pressure transducer assembly 218. FIG. 4C shows struts 250A that form a repetitive curved structure, such as the sinusoidal pattern shown, that allows the struts 250A to absorb stresses in an axial orientation. This in turn allows longitudinal flexing or bending of the pressure transducer assembly 218 at the location of the struts 250A. FIG. 4D shows strut embodiments 250B that have a helical configuration that also allows for longitudinal flexing or bending of the pressure transducer assembly at the struts 250B. The struts 250A and 250B may have the same or similar features, dimensions and materials as those of struts 250. For some embodiments, the aperture 236 and corresponding struts 250 may have a longitudinal length of about 0.1 mm to about 10 mm. The tubular structure of the frame structure 234 may have a wall thickness of about 0.003 inches to about 0.02 inches. For some embodiments, the distance from the distal tip of the distal tissue engaging member 220 to a proximal end 252 of the omni-directional aperture 236 may be about 10 mm to about 20 mm.

Figure 6:
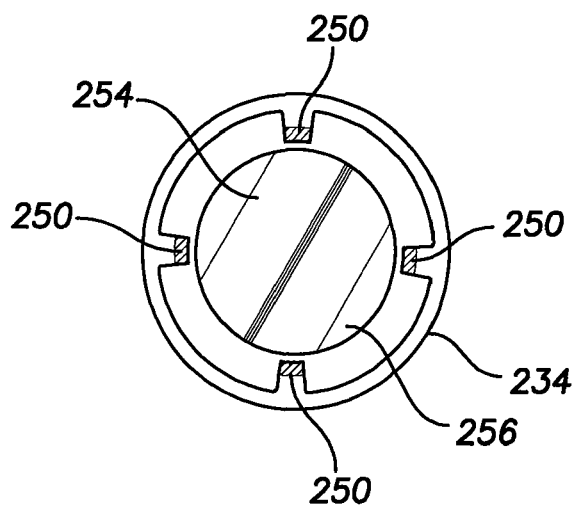
FIG. 6 is a transverse cross sectional view of the lead of FIG. 4 taken along lines 6-6 of FIG. 4.
Figure 7:
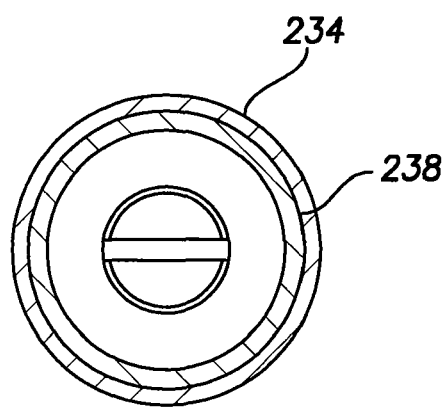
FIG. 7 is a transverse cross sectional view of the lead of FIG. 4 taken along lines 7-7 of FIG. 4.

Although not shown for purposes of illustration in FIG. 4, a pressure wave transmitting material 254 such as a polymer or gel may optionally be disposed within the volume 232 as shown in FIG. 6. The pressure wave transmitting material 254 may be useful to prevent tissue ingrowth or thrombus (clot) formation into the volume 232 after the lead 202 has been deployed within a patient's body so as to allow ongoing consistent pressure measurements at the pressure sensitive surface 228 of the pressure transducer 226. Suitable materials for the pressure wave transmitting material may include biocompatible biostable polymers such as silicone gel, Tecoflex®, Tecothane®, Carbothane®, or biodegradable polymers such as PLGA copolymers or the like. The pressure wave transmitting material 254 may completely or partially fill the volume 232, but should provide a continuous pressure wave transmitting path from substantially all positions disposed about the omni-directional aperture 236 to the pressure sensitive surface 228. An outer surface 256 of the pressure transmitting material 254 may be shaped so as to be substantially flush with the nominal outer surface of the frame structure 234 disposed adjacent the aperture 236. The outer surface of the pressure wave transmitting material 254 may also be coated with a polymeric skin to confine the material 254 to the enclosed volume 232. This may be particularly desirable in embodiments where soft flowable gels are used for the pressure wave transmitting material 254.

The tubular member 248 of the lead body 204 is a flexible hollow member having an inner lumen 258 that may serve to house one or more signal conducting conduits such as wires, fiber optic elements, fluid columns or the like which may be used to conduct signals between the various electrodes 220, 222 and 224 or transducer 226 and the stimulation device 10. The tubular member 248 may be a single lumen extrusion of biocompatible polymer suitable for implantation such as polyurethane or the like. For some embodiments, the lead body 204 may be a flexible elongate member capable of navigation through tortuous body passages, such as the cardiovascular system of a patient, so as to allow percutaneous delivery of the lead 202 to a desired site within a patient's body. For embodiments of the lead 202 configured to be delivered to the right ventricle of a patient, the lead body 204 may have a length of about 45 cm to about 100 cm. The tubular member 248 may have an outer transverse dimension or diameter of about 1.5 mm to about 4 mm for some embodiments.

An inner tubular member 262 may be disposed within the inner lumen 258 of the tubular member 248 that has an inner lumen 264 for accepting passage of a torquing stylet 266 that is used to transmit torque from the proximal end of the lead 202 to the distal end of the lead 202 and ultimately to the helical tissue engaging member 220. Referring to FIGS. 4A and 4B, the stylet 266 is an elongate member made of a high strength material and capable of transmitting torque from a knurled knob 267 at a proximal end of the stylet 266 to along the length of the stylet 266 to a distal tip 268 of the stylet 266. The stylet 266 may be made of high strength materials such as stainless steel, MP35N and the like and may have a nominal transverse dimension or diameter of about 0.01 inches to about 0.025 inches. The length of the stylet 266 should be greater than that of the lead body 204. This length allows the proximal end of the stylet 266 to extend beyond the proximal end of the proximal connector of the lead 202 with the distal tip 268 of the stylet 266 engaged with the keyed socket 272 of the lead 202.

Efficient transmission of torque from the proximal end of the lead 202 to the distal end or portion of the lead 202 may be useful in deploying the helical tissue engaging member 220 into target tissue during deployment of the lead 202. The stylet 266 used to improve the torque transmission may have a distal tip 268 which is shaped to engage the keyed socket 272 in a distal bulkhead member 274 in a torque transmitting configuration in order to transmit torque from the distal end 268 of the stylet 266 to the distal section of the lead 202. The keyed socket 272 is configured to reversibly engage the distal end 268 of the stylet 266 in a torque transmitting relationship. The distal bulkhead member 274 is disposed within the inner lumen 258 of the tubular member 248 at a distal end of the tubular member 248 and is secured to an inner wall or surface of the inner lumen of the tubular member. The outer surface 278 of the tubular member 248 at the distal end 275 of the tubular member 248 is secured to a proximal portion of the frame structure 234. As such, torque applied to the knurled knob 267 at the proximal end 282 of the stylet 266 is transmitted through the stylet 266, distal bulkhead member 274 and distal end 275 of the tubular member 248 to the frame structure 234. Torque applied to the proximal end 282 of the stylet 266 is thereafter transmitted through the frame structure 234 and a distal header element 284 to the distal tissue engaging member 220.

The distal helical tissue engaging member 220 is secured to the distal header element 284 which fills the inner lumen of the distal portion of the tubular structure of the frame structure 234 distal of the pressure transducer 226. The distal header element 284 may be a solid piece of material shaped or machined to fit within the frame structure 234 or may be a moldable or curable material such as an epoxy or other type of high durometer polymer that may be molded or otherwise shaped to fit within the distal portion of the frame structure 234. The distal header element 284 has rounded distal edges to form an atraumatic tip to prevent damage to tissue contacted by the distal end 208 of the lead 202. The distal tissue engaging member 220 is secured to the distal header element 284 by potting of a proximal end 286 of the tissue engaging member 220 into the distal header element 284. The tissue engaging member 220 is substantially centered radially with respect to the distal end 208 of the lead 202 such that a longitudinal axis of the tissue engaging element 220 is substantially collinear with the longitudinal axis 212 of the distal portion of the lead 202.

For some embodiments of the lead 202, it may be desirable to deliver bioactive agents, such as drugs and the like, from the distal portion of the lead 202. For example, it may be desirable to deliver one or more anti-inflammatory agents such as a corticosteroid, including dexamethasone, or anti-proliferative/anti-inflammatory drugs such as Paclitaxel®, Sirolimus® Everolimus®, Pmicrolimus® or the like from the distal portion of the lead 202. As such, the pressure wave transmitting material 254, the frame structure 234 including struts 250, the material of the distal header element material 284, or all, may include a drug eluting material, such as a drug eluting polymer co-polymer that is configured to elute such bioactive agents after deployment of the lead 202 into a patient's body over a predetermined period of time. The drug eluting material may be coated or layered in multiple coatings of the same or differing drug eluting materials on an outside surface of any of these structures 254, 234, 250, 284, as well as others. In addition, these structures, 254, 234, 250 and 284 may include holes or cavities which contain drug eluting materials and are configured to hold these materials and allow elution of same to occur over time. Some suitable drug eluting polymers may include bioerrodable polymers PLGA, or any biostable polymer that can be loaded with suitable bioactive agents such as used with drug eluting stents including Taxus® manufactured by Boston Scientific or Cypher® manufactured by Johnson and Johnson as well as others. The elution of some of these agents may be useful in preventing or reducing complications from tissue inflammation caused by contact of the lead 202, and, particularly, the distal end 208 and distal tissue engaging member 220 of the lead 202 with tissue. Inflammation, scarring and other tissue reactions that result from tissue insult as a result of deployment of the lead 202 can reduce or otherwise change the conductivity of the affected tissue and complicate or prevent the administration of cardiac pacing therapy from an electrode adjacent such tissue. The elution of some of these agents may also be useful for reducing or preventing tissue overgrowth or thrombus formation on the frame structure 234 or aperture 236, particularly in embodiments that do not include pressure wave transmitting material 254 in the volume 232.

This distal tissue engaging member 220, which may also be configured to act as an electrode, such as a pacing electrode, may be made of suitable high strength materials such as stainless steel, MP35N, tungsten and the like. Because the distal tissue engaging member 220 may also serve as an electrode, it may also be useful for some embodiments of the distal tissue engaging member to include a low polarization coating such as titanium nitride on the tissue engaging member 220. Radiopaque coatings or materials incorporated into the distal tissue engaging member may also be useful. Some embodiments of the distal tissue engaging member may have a length that extends distally beyond the distal end 208 of the lead body 204 of about 1 mm to about 3 mm. The pitch of the coiled structure of the distal tissue engaging member may be about 0.5 turns per mm to about 3 turns per mm.

The proximal end 286 of the distal tissue engaging member 220 is electrically coupled to a signal conducting conduit 288 in the form of an insulated wire that extends from the distal tissue engaging member proximally through the frame structure 234 and the inner lumen 258 of the tubular member 248 of the lead body 204. The signal conducting conduit 288 is coupled to the distal tissue engaging element 220 and terminates proximally at a corresponding conductive terminal on the proximal connector 214 of the lead 202. The conductive terminal on the proximal connector 214 may then be coupled to the appropriate signal generating circuitry of the stimulation device 10.

The distal shocking electrode 222 is disposed on the outside surface of the tubular member 248 of the lead body 204 and includes a conductive element 292 in a coiled structure having an electrically conductive outer surface. Suitable materials for the distal shocking electrode 222 include stainless steel, tungsten and the like. Some embodiments of the distal shocking electrode 222 may have an overall axial length of about 1 mm to about 15 mm and an outer diameter or transverse dimension of about 1 mm to about 5 mm. Some embodiments of the distal shocking electrode 222 may have an outer exposed conductive surface area of about 10 $mm^2$ to about 100 $mm^2$. The distal shocking electrode 222 may also include a low polarization coating (not shown), such as the low polarization coatings discussed above for use with regard to the distal tissue engaging member 220 and is coupled to a conductive terminal on the proximal connector 214 by a signal conducting conduit 300, such as an insulated wire. The proximal shocking electrode 224 shown in FIG. 3 may have the same or similar features, materials or dimensions as those of the distal shocking electrode 222 and may be coupled to a conductive terminal of the proximal connector 214 by a signal conducting conduit (not shown).

Figure 8:
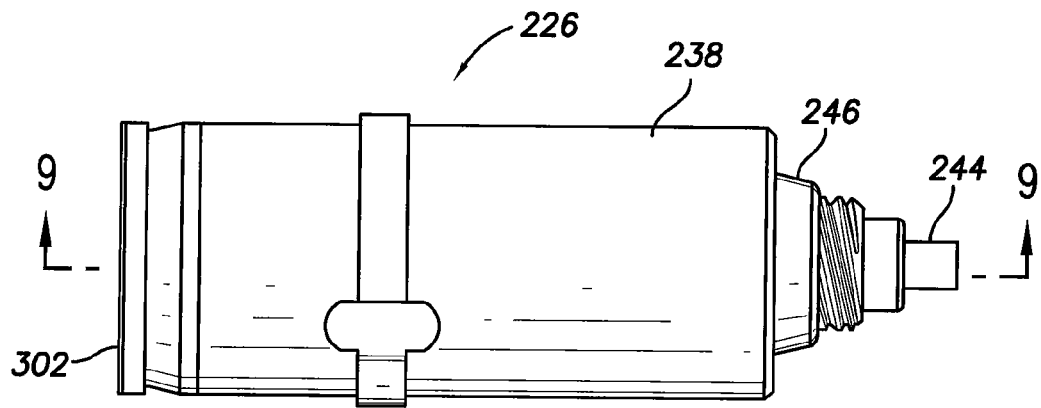
FIG. 8 is an elevational view of an embodiment of a pressure transducer.
Figure 9:
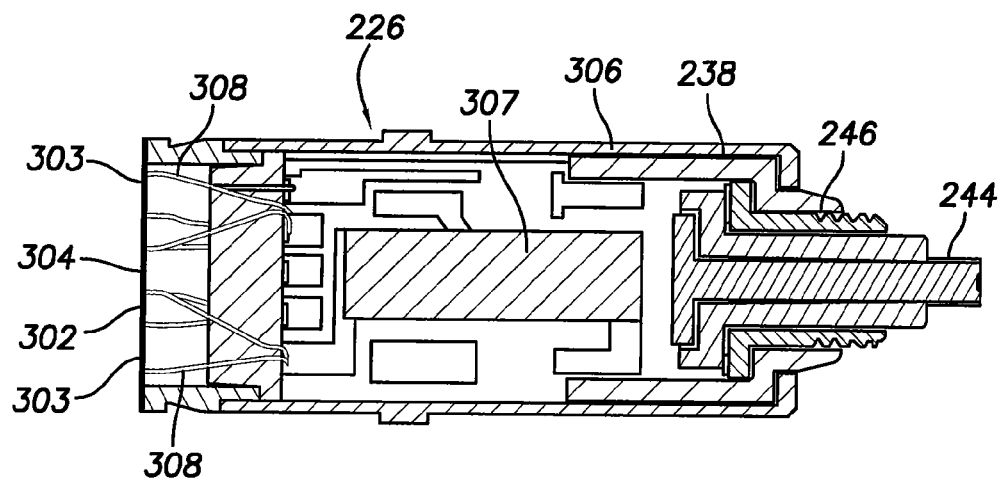
FIG. 9 is an elevational view in longitudinal section of the pressure transducer of FIG. 8.

Referring to FIGS. 8 and 9, an embodiment of the pressure transducer 226 is shown in more detail. The internal transducer components of the pressure transducer 226 including the transducer element, power, and communications components are enclosed in a hermetic casing or housing 238. For some embodiments, the casing 238 comprises metal, ceramic, or glass, alone or in combination, or other constituents for constructing hermetic packaging. A hermetically sealed titanium housing 238 may be desirable for some embodiments of the transducer 226. The transducer housing 238 has proximal and distal ends and the distal end of the housing 238 may include at least one circular hermetic diaphragm 302. The diaphragm material may also include titanium for some embodiments, having an inner surface opposite the pressure sensitive surface 228 and designed to translate or flex in response to pressure changes at the desired location. For some embodiments, the diaphragm or membrane 302 is mechanically coupled to the transducer components which are enclosed by the housing 238.

For some embodiments, the enclosed transducer components include semiconductors that control power, pressure signal transduction, local signal processing, and data telemetry. Resistive strain gauges 303, 304 may be bonded, or otherwise coupled, to the inside surface of the diaphragm 302. The pressure transducer 226 may also include an application-specific integrated circuit (ASIC) 307 or "measurement electronics." Measurement electronics 307 are contained within the housing 238 and electrically connected to the strain gauges by fine gold wires 308 or other means of electrical connection. The proximal end of the housing 238 is sealed by a zirconia ceramic feed-through 246 that is brazed to the titanium cylinder of the housing 238. The housing 238 may contain a gaseous atmosphere, such as an inert gaseous atmosphere, of helium, argon, or any other suitable gas or combination of gases. For some embodiments, an electrical insulating liquid such as an oil or other electrically insulating liquids may be disposed within the housing. The housing 238 may also be evacuated prior to sealing For some embodiments, the pressure transducer 226 contains an internal power source, such as a battery. For some embodiments, the pressure transducer 226 may be powered transcutaneously by induction of radio frequency current in an implanted wire coil (not shown) connected directly to the pressure transducer 226 or connected by a flexible lead containing electrical conductors, to charge an internal power storage device such as a capacitor.

The housing 238 of the pressure transducer 226 may be provided in a wide range of sizes and shapes. For some embodiments, the housing 238 may be about 1 mm to about 5 mm long, and about 2 mm to about 4 mm in diameter or outer transverse dimension. For some embodiments, the housing 238 may be about 5 mm to about 15 mm long. In another embodiment, the housing 238 is about 8 mm long, and about 3 mm in diameter. For some embodiments, the housing 238 is less than about 10 mm long. For some embodiments, the housing 238 may be rectangular, square, spherical, oval, elliptical, or any other shape suitable for incorporation into lead 202.

It may be desirable for reliable pressure wave measurements to configure the pressure transducer 226 so as to minimize the effect of viscoelastic drift on such measurements. Viscoelastic drift is an effect that may have a negative effect on the accuracy or reliability of some pressure transducer. For example, after prolonged exposure to a large change in average ambient pressure, such as the change to lower pressures during travel to high altitude, some pressure transducers undergo viscoelastic drift whereby their components undergo elastic deformation with prolonged time constants lasting hours to days or more before returning to the pre-stressed state. This phenomenon may result in a baseline shift that persists until another large change in average ambient pressure sets into motion another viscoelastic drift to another new baseline. In order to address this problem, for some embodiments of the pressure transducer 236 shown, the viscoelastic properties of the pressure transducer 236 are characterized during pre-implant calibration. For some embodiments, the known viscoelastic properties are used in combination with the recorded pressure variations over time to obtain pressure measurements that are corrected for viscoelastic drift.

For the pressure transducer embodiments 226 shown in FIGS. 8 and 9, two sets of adherent strain gauges are used, an inner set 304 near the center of the diaphragm 302 where tangential strain is relatively high and an outer set 303 near the periphery of the diaphragm where radial strain is also high but of opposite polarity. Electrically, this arrangement is connected to form a Wheatstone bridge circuit. In order to make the overall transducer relatively small, compromises are made on the supporting structure of the diaphragm. Because the supporting structure is not absolutely rigid, forces applied to the side of the structure will result in a small deformation of the diaphragm. The radial strain gauges are the most affected by this "side load." As such, the radial strain gauges may be oriented 90 degrees from each other which results in a partial canceling of the side load force effects, as the signal effects are substantially subtractive rather than additive.

For some other pressure transducer 226 embodiments, an inner surface opposite the outer pressure sensitive surface 228 of a diaphragm 302 of the pressure transducer 226 has a plurality of resistive strain gauges coupled thereto. Two or four resistive strain gauges 303, 304 may be adhered to an internal surface of the diaphragm 302 by an adhesive that may serve several functions including fixation of the strain gauges to the diaphragm and electrical insulation of the strain gauges to prevent a short circuit to the case of the pressure transducer 226. In order to achieve electrical insulation of the strain gauges, the adhesive may need to be of a thickness that is substantial enough to exhibit some viscoelastic displacement in response to a change in the shape of the diaphragm 302, resulting in transducer drift in response to large prolonged change in average pressure. As such, a silicon dioxide insulation layer may be grown on the bottom of the silicon strain gauges providing additional electrical isolation and consequently minimizing the thickness of adhesive and resulting viscoelastic drift.

For some other pressure transducer 226 embodiments, a software algorithm may be used to automatically correct for viscoelastic drift. For yet some other embodiments, a secondary diaphragm may be located on other portions of the transducer 226. The secondary diaphragm is used to measure pressure at a second site or to measure a differential pressure between the distally located diaphragm 302 and the secondary diaphragm. The second diaphragm may be used to provide additional calibration information for the first diaphragm 302, and/or vice versa. In still other embodiments, a diaphragm that is both essentially non-compliant and essentially flat is used to minimize the effects of tissue overgrowth on reducing transducer gain (non-compliance), while optimizing intrinsic gain (flatness). Diaphragm thickness may be maximized in order to maximize flatness and minimize compliance, consistent with the sufficient compliance to derive a useable transducer signal.

In some embodiments, the pressure transducer 226 includes temperature compensation so that pressure measurements will be minimally affected or unaffected by temperature change. For some embodiments, an apparatus to measure the temperature at the site of the pressure transducer 226 is provided. For some embodiments, temperature compensation or modulation is achieved by using multiple resistive strain gauges arranged in a Wheatstone bridge, such that the electrical voltage output of the Wheatstone bridge is proportional to the ratio of two or more resistances. By selecting resistive strain gauges with substantially identical temperature coefficients, the intrinsic output of the bridge is made to be temperature independent.

Another embodiment of temperature compensation utilizes an internal thermometer, such as a thermistor, which is placed in a location isolated from the transducer diaphragm 302 so that its resistance does not depend on pressure variations. Prior to implanting or otherwise deploying the lead 202 and the pressure transducer 226, calibration data is collected consisting of the output of the transducer 226 versus pressure as a function of the reading of the internal thermometer. After implantation, the signal from the internal thermometer is used together with the output from the pressure transducer 226 and the calibration data to determine the temperature compensated pressure reading. In addition, a band gap voltage reference may be used to create a current proportional to absolute temperature that is then compared to the temperature independent voltage reference. Embodiments of pressure sensors and transducers having features, dimensions and materials that may be incorporated into any of the pressure transducer embodiments discussed herein are disclosed in U.S. patent application Ser. No. 11/115,991, publication number U.S. 2005/0288722, filed Apr. 27, 2005, by Eigler et al. titled "Implantable Pressure Transducer System Optimized for Anchoring and Positioning" which is incorporated by reference herein in its entirety.

As discussed above, the cardiac rhythm management system 200 may be used for pacing, sensing, defibrillation, and pressure sensing within a patient's heart. In addition, such systems may be used for treating a variety of indications including administration of cardiac resynchronization therapy. The system 200 may be deployed in a patient's body using percutaneous delivery methods. For example, referring to FIG. 10, access to a patient's vasculature may initially achieved through an introducer sheath (not shown) using a standard Seldinger technique or the like. For embodiments of the lead 202 which are to be deployed in the right ventricle 312, the lead 202 may be advanced through the patient's vasculature through the SVC, into the right atrium and then into the right ventricle of the patient's heart.

Figure 10:
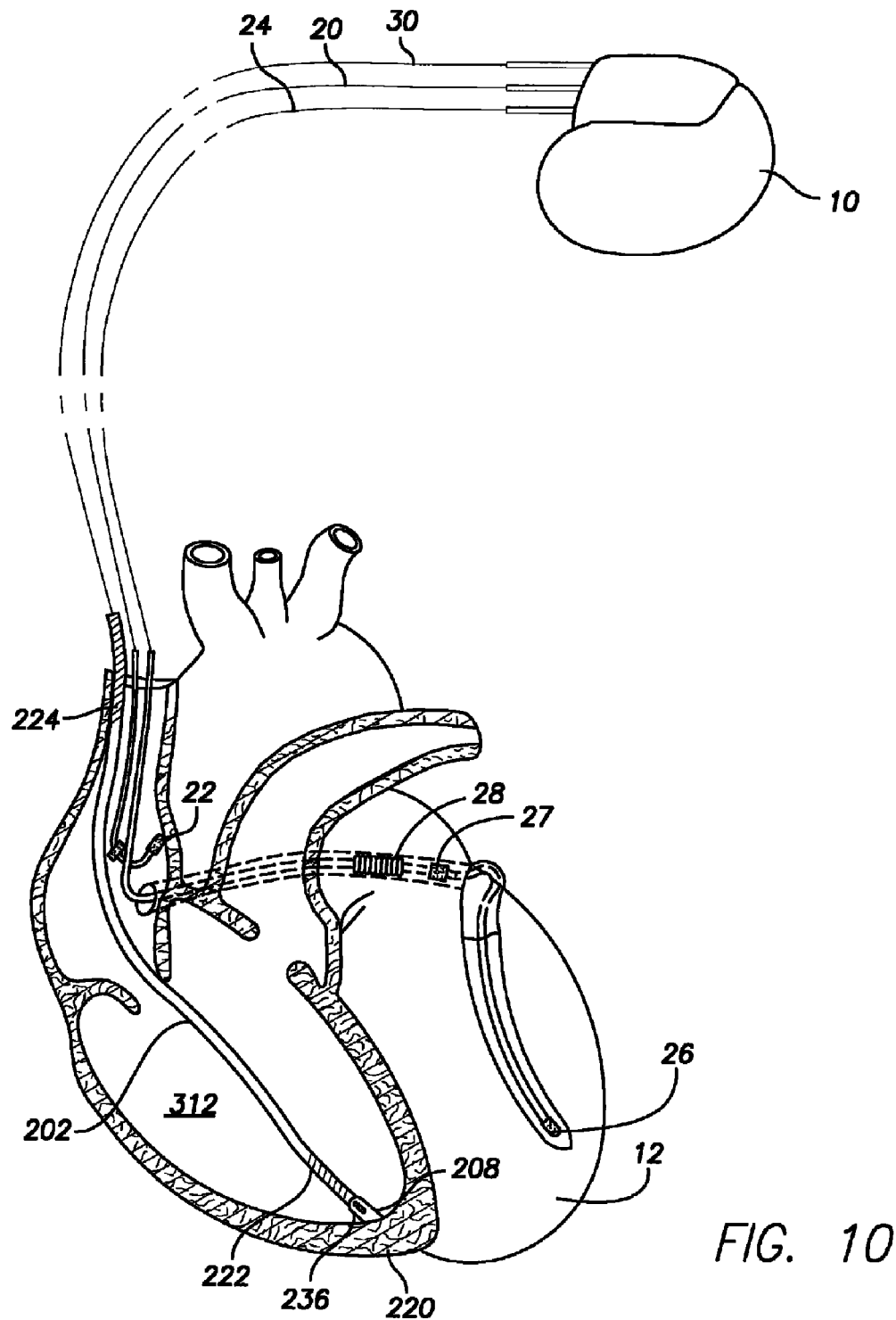
FIG. 10 is a perspective view in partial section of an embodiment of a cardiac rhythm management system embodiment deployed within a patient's heart.

Once in the right ventricle 312, the distal tissue engaging member 220 may then be advanced until contacting a desired tissue site for securing the distal tissue engaging member. The stylet 266 may then be advanced into the inner lumen 264 of the inner tubular member 262 until the distal tip 268 of the stylet 266 engages the socket 272 of the bulkhead member 274. Thereafter, torque and an axial force in the distal direction is applied to the knurled proximal knob 267 and subsequently to the distal portion of the lead 202. The torque and axial force applied to the distal portion of the lead 202 results in rotation of the distal portion of the lead towards the target tissue site and sharp tissue penetrating tip 221 of the distal tissue engaging member 220 thereby screws and distally advances into the target tissue so as to become secured to the desired target tissue site. Once the distal tissue engaging member 220 is screwed into the target tissue site, the stylet 266 may then be withdrawn proximally from the inner tubular member 262. FIG. 10 shows an embodiment of a cardiac rhythm management system 200 with the distal tissue engaging member 220 secured to target tissue of the right ventricle 312 of a patient and coupled to the stimulation device 10. The stimulation device 10 is coupled to the lead 202 to allow the communication of sensed electrical signals and pressure wave signals from the patient's body between the lead 202 and the stimulation device 10. The coupling also allows for the delivery of therapeutic electrical signals, such as pacing and shocking electrical signals, from the stimulation device 10 to the electrodes of the lead 202.

Once so deployed, the cardiac rhythm management system 200 may be used to deliver rhythm management therapy signals such as pacing therapy signals from the stimulation device 10 to the patient's heart tissue through the distal tissue engaging member 220, the housing 238 of the pressure transducer 226 or any other electrode of the lead 202. Therapy signals such as shocking therapy signals may be delivered from the stimulation device 10 to the patient's heart tissue through either or both of the distal shocking electrode 222 or proximal shocking electrode 224. Any of the electrodes of the lead 202 may also be used to sense or detect electrical information or signals generated by the patient's heart tissue by the stimulation device 10 which may be configured and programmed to analyze the sensed signals and store the information or use the information to adjust therapy signal parameters. The additional leads 20 and 24 shown in FIG. 10 are for RA and LV pacing and may optionally be eliminated in some pacing configurations.

Pressure measurements may also be taken within the patient's right ventricle 312 during administration of the rhythm management therapy or at any other suitable time. For example, pressure measurements may be taken or detected during the deployment process of the lead 202 or at any time after deployment. Pressure wave signals within the patient's body adjacent the distal portion of the lead 202 may propagate from a position outside the distal portion of the lead through the omni-directional aperture 236 and optional pressure wave transmitting material 254 and onto the pressure sensitive surface 228 of the pressure transducer 226. It should be noted that any of the pressure measurements or therapy discussed above may also optionally be carried out with the lead 202 of the system 200 in a desired position within the patient's body, but without the distal tissue engaging member 220 secured to target tissue.

FIGS. 11-14 illustrate a distal portion of an embodiment of a lead 202A which is configured to be coupled to stimulation device 10, in an embodiment of a cardiac rhythm management system 200A. Lead 202A includes distal tissue engaging member 220 disposed in a configuration which allows the distal tissue engaging member 220 to be withdrawn axially in a proximal direction into a distal lumen 314 during deployment. The pressure transducer assembly 218 disposed on the distal section 210 of the lead body 204A may be similar to or the same as the pressure transducer assembly 218 discussed above. The pressure transducer assembly 218 includes the pressure transducer 226 with a pressure sensitive surface 228, a volume 232 adjacent the pressure sensitive surface 228 enclosed by a frame structure 234 having an omni-directional aperture 236 disposed substantially about an entire circumference of the lead body 204, and, more specifically, disposed substantially about the entire circumference of the frame structure 234. The aperture 236 is configured to allow pressure signals or pressure waves to enter the volume 232 from a position outside the lead 202 and interact with the pressure sensitive surface 228 of the transducer 226.

Lead 202A does not have an inner tubular member 262 but instead has a stylet lumen 316 that is secured to and extends along an outer surface of the pressure transducer assembly 218. A proximal portion of the stylet lumen 316 may be formed into the tubular member 248A of the lead body 204A which may be configured as a dual lumen extrusion or the like. The stylet lumen 316 is configured to slidingly accept the stylet 266 discussed above as it is axially advanced in a distal direction within the stylet lumen 316. At a distal end of the stylet lumen 316, a socket member 318, which is disposed on and secured to a proximal end of the tissue engaging member 220, is disposed within the stylet lumen 316 and includes a keyed socket 320. The keyed socket 320 is configured to couple to the distal tip 268 of the stylet 266 in a torque transmitting relationship.

The socket member 318 may include an electrically conductive material that has an outer radial surface 322 configured to mechanically and electrically couple to an inner surface 324 of a cylindrical sleeve 326 disposed about a distal end of the distal lumen 314. The cylindrical sleeve 326 may in turn be coupled to a corresponding conductive terminal of the proximal connector 214 by a signal conducting conduit, such as insulated wire 328. The lead 202A may have the same or similar features, dimensions and materials as those of lead 202 discussed above.

In use, the lead 202A may be deployed and used in substantially the same manner as lead 202. The distal tissue engaging member 220 is, however, withdrawn into the distal lumen during deployment until the distal end 208A of the lead 202A is in close proximity to target tissue. Once so positioned, the stylet 266 may be advanced axially in the stylet lumen 316 until the distal tip 268 of the stylet 266 engages the keyed socket 320 of the socket member 318 in a torque transmitting configuration. The stylet 266 may then be distally advanced and rotated so as to distally advance and rotate the distal tissue engaging member 220 relative to the pressure transducer assembly 218. As the distal tissue engaging member 220 is axially advanced in a distal direction and rotated, the sharp tissue penetrating tip of the distal tissue engaging member 220 penetrates the tissue and the helical structure of the distal tissue engaging member screws into the tissue. After the distal tissue engaging member 220 is secured to the target tissue, the stylet 266 may be disengaged from the keyed socket 320 and proximally withdrawn from the stylet lumen 316. Alternatively, the stylet 266 may be engaged with the keyed socket 320 while the lead 202A is being advanced during deployment. Once the lead 202A is deployed in position, with the distal tissue engaging member 220 secured to target tissue, the lead 202A may then be used in the same or similar manner to use of lead 202 discussed above. Lead 202A may optionally also be used without the distal tissue engaging member engaged with target tissue.

Figure 15:
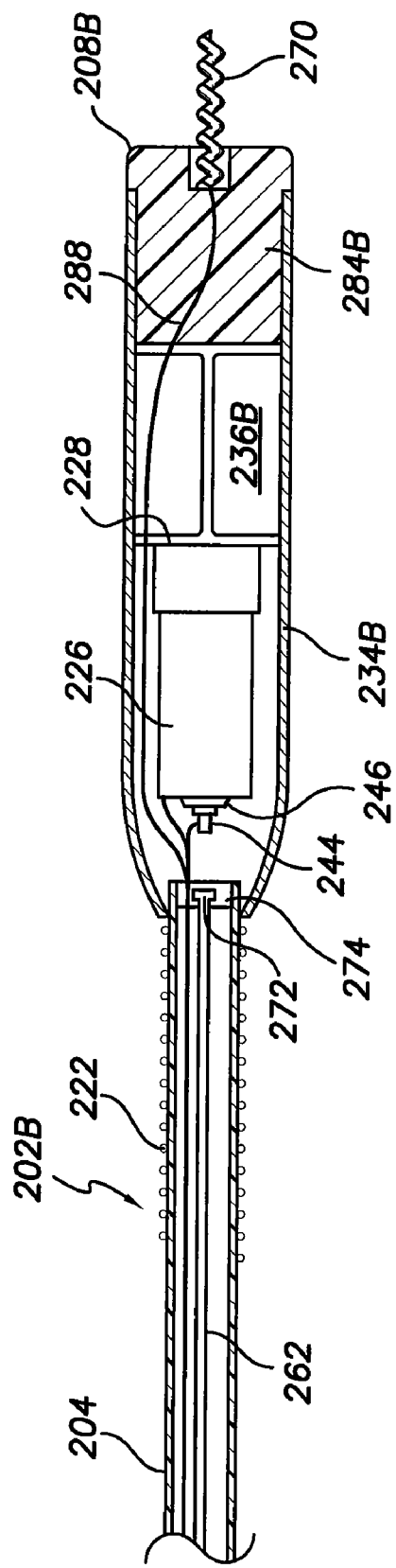
FIG. 15 is an elevational view in partial section of a distal portion of an embodiment of a lead having a pressure sensitive surface facing a substantially distal direction.

FIG. 15 illustrates a distal portion of an embodiment of a lead 202B that may be deployed and used in substantially the same manner as lead 202 and coupled to stimulation device 10 of a cardiac rhythm management system 200B. In addition, the lead 202B may have the same or similar features, dimensions and materials as those of lead 202 discussed above. With regard to lead 202B, the pressure sensitive surface 228 of the pressure transducer 226 is substantially perpendicular to the longitudinal axis 212 of the distal portion of the lead 202B and forms a proximal boundary for the volume 232B enclosed by the frame structure 234B.

For lead embodiment 202B, the pressure sensitive surface 228 is facing the distal direction instead of the proximal direction, as is the case with the lead 202 embodiment of FIGS. 4-9. The pressure transducer assembly 218B is disposed on the distal section 210 of the lead body 204B and includes the pressure transducer 226 with the pressure sensitive surface 228, a volume 232B adjacent the pressure sensitive surface 228 enclosed by the frame structure 234B having an omni-directional aperture 236B disposed substantially about an entire circumference of the lead body 204B. The aperture 236B is configured to allow pressure signals or pressure waves to enter the volume 232B from a position outside the lead 202 and interact with the pressure sensitive surface 228 of the transducer 226.

The volume 232B may be filled with the pressure wave transmitting material 254 (not shown) that may have an outer surface that is substantially flush with a nominal outer surface of the frame structure 234B. Distal header element 284B fills the space within a distal portion of an inner lumen of the frame structure 234B and secures the proximal end of the distal tissue engaging member 220 to the distal end 208B of the lead 202B. The distal header element 284B forms the distal end 208B of the lead 202B and may include the same materials and features as those of the distal header element 284. The structure of lead 202B is similar in many respects to the structure of lead 202, however, the structure of lead 202B may allow the omni-directional aperture 236B to be disposed more closely to the distal end 208B of the lead 202B than would be possible for lead 202. This configuration may be particularly useful for some indications.

In general, a wide variety of techniques can be implemented consistent with the principles the invention and no attempt is made herein to describe all possible techniques. Although described primarily with reference to embodiments wherein the implanted stimulation device is a defibrillation/pacer, the principles discussed herein are applicable to other implantable medical devices as well. The various functional components of the exemplary embodiments may be implemented using any appropriate technology including, for example, microprocessors running software programs or application specific integrated circuits (ASICs) executing hard-wired logic operations. With regard to the above detailed description, like reference numerals used therein refer to like elements that may have the same or similar dimensions, materials and configurations. While particular forms of embodiments have been illustrated and described, various modifications can be made without departing from the spirit and scope of the embodiments of the invention. Accordingly, it is not intended that the invention be limited by the forgoing detailed description.

What is claimed is:

1. An implantable lead comprising:
an elongate flexible lead body having a distal portion, a distal end, a proximal end and an longitudinal axis, wherein the proximal end is configured to be coupled to an implantable medical device;
an electrode disposed on the lead body; and
a pressure transducer assembly disposed at the distal portion of the lead body having a pressure transducer with a pressure sensitive surface, a volume adjacent the pressure sensitive surface enclosed by a frame structure defining a plurality of apertures circumscribing a circumference of the lead body, the apertures allowing pressure waves to enter the volume from outside the lead and to interact with the pressure sensitive surface of the transducer, wherein the pressure sensitive surface of the pressure transducer comprises a diaphragm surface contained within the lead body located distal of the plurality of apertures and oriented substantially perpendicular to the longitudinal axis of the lead body facing the volume enclosed by the frame structure.

2. The lead of claim 1 wherein a proximal extremity of the plurality of apertures is disposed about 5 mm to about 20 mm from the distal end of lead body.

3. The lead of claim 1 further comprising a helical tissue engaging member having a sharpened tissue penetrating distal tip.

4. The lead of claim 3 wherein the helical tissue engaging member comprises a pacing electrode.

5. The lead of claim 1 further comprising a gel material disposed within the volume enclosed by the frame structure and in contact with the diaphragm surface of the pressure transducer to prevent tissue in-growth into the volume.

6. The lead of claim 1 further comprising a connector disposed at a proximal end of the lead body and having at least two conductive terminals coupled respectively to the electrode and pressure transducer and wherein the connector is configured to couple to an implantable stimulation device with pressure sensing capability.

7. The lead of claim 6 further comprising conductor cables in electrical communication between the electrode, the pressure transducer and respective conductive terminals of the connector.

8. The lead of claim 1 further comprising at least one large surface area shocking electrode disposed on an outer surface the lead body proximal of the plurality of apertures.

9. The lead of claim 1 further comprising at least two large surface area shocking electrodes disposed at an outer surface of the lead body proximal of the plurality of apertures and axially separated from each other along the longitudinal axis of the lead body.

10. The lead of claim 1 wherein the electrode includes a low polarization coating.

11. An implantable pressure sensing lead comprising:
    an elongate flexible lead body having a distal portion, distal end, a proximal end and a longitudinal axis, wherein the proximal end is configured to be coupled to an implantable medical device;
    a distal tissue engaging member configured as a helical electrode having a tissue penetrating distal tip extending from the distal end of the lead body;
    a pressure transducer assembly disposed at the distal portion of the lead body having a pressure transducer with a pressure sensitive surface, volume adjacent the pressure sensitive surface enclosed by a frame structure defining a plurality of apertures circumscribing a circumference of the lead body, the apertures allowing pressure waves to enter the volume from outside the lead and to interact with the pressure sensitive surface of the transducer, wherein the pressure sensitive surface of the pressure transducer comprises a diaphragm surface contained within the lead body located distal of the plurality of apertures and oriented substantially perpendicular to the longitudinal axis of the lead body facing the volume enclosed by the frame structure;
    a first large surface area shocking electrode disposed on the lead body proximal of the pressure transducer assembly; and
    a second large surface area shocking electrode disposed on the lead body proximal of the first large surface area shocking electrode.

12. The lead of claim 11 wherein a proximal extremity of the plurality of apertures is disposed about 5 mm to about 20 mm from the distal end of lead body.

13. The lead of claim 11 further comprising a gel material disposed within the volume enclosed by the frame structure and in contact with diaphragm surface of the pressure transducer to prevent tissue in-growth into the volume.

14. The lead of claim 11 wherein the electrode includes a low polarization coating.

15. An implantable cardiac rhythm management system comprising:
    an elongate flexible lead body having a distal portion, distal end, a proximal end and a longitudinal axis, wherein the proximal end is configured to be coupled to an implantable medical device;
    a tissue engaging member disposed at the distal end of the lead body;
    an electrode disposed on the distal section of the lead body; and
    a pressure transducer assembly disposed at the distal portion of the lead body having a pressure transducer with a pressure sensitive surface, a volume adjacent the pressure sensitive surface enclosed by a frame structure defining a plurality of apertures circumscribing a circumference of the lead body, the apertures allowing pressure waves to enter the volume from outside the lead and to interact with the pressure sensitive surface of the transducer, wherein the pressure sensitive surface of the pressure transducer comprises a diaphragm surface contained within the lead body located distal of the plurality of apertures and oriented substantially perpendicular to the longitudinal axis of the lead body facing the volume enclosed by the frame structure; and
    an implantable stimulation device coupled to the lead and configured to monitor pressure and provide electrical cardiac stimulation signals to the electrode to manage a cardiac rhythm of the patient.

16. The system of claim 15 wherein a proximal extremity of the plurality of apertures is disposed about 5 mm to about 20 mm from the distal end of lead body.

17. The system of claim 15 further comprising a gel material disposed within the volume enclosed by the frame structure and in contact with the diaphragm surface of the pressure transducer to prevent tissue in-growth into the volume.

* * * * *